US012575911B2

(12) United States Patent
Zellermayer

(10) Patent No.: US 12,575,911 B2
(45) Date of Patent: Mar. 17, 2026

(54) DISTRACTOR, BONE SCREW FOR SAID DISTRACTOR, AND METHOD FOR PRODUCING SAID DISTRACTOR

(71) Applicant: Elmar Gregor Zellermayer, Wels (AT)

(72) Inventor: Elmar Gregor Zellermayer, Wels (AT)

( * ) Notice: Subject to any disclaimer, the term of this patent is extended or adjusted under 35 U.S.C. 154(b) by 217 days.

(21) Appl. No.: 17/782,971

(22) PCT Filed: Dec. 4, 2020

(86) PCT No.: PCT/AT2020/060435
§ 371 (c)(1),
(2) Date: Jun. 6, 2022

(87) PCT Pub. No.: WO2021/108828
PCT Pub. Date: Jun. 10, 2021

(65) Prior Publication Data
US 2023/0018609 A1     Jan. 19, 2023

(30) Foreign Application Priority Data

Dec. 5, 2019   (AT) .............................. A 60268/2019
Feb. 27, 2020   (AT) .............................. A 60050/2020

(51) Int. Cl.
*A61C 7/10*          (2006.01)
*A61B 17/66*        (2006.01)
*A61C 7/00*          (2006.01)

(52) U.S. Cl.
CPC .............. *A61C 7/10* (2013.01); *A61B 17/663* (2013.01); *A61C 7/002* (2013.01)

(58) Field of Classification Search
CPC ............. A61C 7/10; A61C 7/002; A61C 7/00; A61B 17/663; A61B 17/66; A61B 17/60; A61B 17/58; A61B 17/56
(Continued)

(56) References Cited

U.S. PATENT DOCUMENTS

2009/0136920 A1     5/2009   Golz et al.
2013/0252195 A1*   9/2013   Popat ........................ A61C 7/10
                                                                                433/7
(Continued)

FOREIGN PATENT DOCUMENTS

DE        102016121296 A1     5/2018
WO          2008011698 A2     1/2008
(Continued)

OTHER PUBLICATIONS

Simon Graf, CAD-CAM design and 3-dimensional printing of mini-implant retained orthodontic appliances, American Journal of Orthodontics and Dentofacial Orthopedics, Dec. 2018, vol. 154, Issue 6 (Year: 2018).*
(Continued)

*Primary Examiner* — Eric J Rosen
*Assistant Examiner* — Mirayda A Aponte

(57) ABSTRACT
A distractor for palatal expansion is disclosed. A high degree of treatment safety can be insured if anchoring parts each have at least two tooth supports and each subsection has at least one of the tooth supports and at least one of the palate rests to which this tooth support is connected in order to thus fix the support surfaces in their position against the palate.

16 Claims, 5 Drawing Sheets

(58) Field of Classification Search
USPC ............................................................. 433/7
See application file for complete search history.

(56) References Cited

U.S. PATENT DOCUMENTS

| | | | |
|---|---|---|---|
| 2015/0056566 A1 | 2/2015 | Moon | |
| 2016/0270883 A1* | 9/2016 | Yousefian | ................ A61C 7/10 |
| 2016/0270884 A1 | 9/2016 | Yousefian | |
| 2017/0079747 A1* | 3/2017 | Graf | ........................ A61P 31/04 |
| 2018/0110592 A1* | 4/2018 | Kanaan | .................... A61C 7/10 |

FOREIGN PATENT DOCUMENTS

| | | | |
|---|---|---|---|
| WO | 2016034973 A1 | 3/2016 | |
| WO | WO-2018139690 A1 * | 8/2018 | |

OTHER PUBLICATIONS

Moon Won. "Class III treatment by combining facemask (FM) and maxillary skeletal expander (MSE)" Seminars in Orthodontics, US, vol. 24, No. 1, Mar. 2018 (Mar. 2018), pp. 95-107 DOI: 10.1053/j.sodo.2018.01.009 ISSN: 1073-8746, XP055780953.

OrthoLab Laboratories. "Power Expanders", Internet, Aug. 30, 2019 (Aug. 30, 2019), pp. 1-1, Retrieved from the Internet: https://www.facebook.com/LaboratoriosOrthoLab/photos/a.1402032640061521/2343591289238980/?type=3&theater [retrieved on Mar. 4, 2021] XP055782221.

Graf Simon et al. "CAD-CAM design and 3-dimensional printing of mini-implant retained orthodontic appliances" American Journal of Orthodontics & Dentofacial Orthopedics, vol. 154, No. 6, Dec. 2018 (Dec. 2018), pp. 877-882.

* cited by examiner

DISTRACTOR, BONE SCREW FOR SAID DISTRACTOR, AND METHOD FOR PRODUCING SAID DISTRACTOR

FIELD OF THE INVENTION

The invention relates to a distractor for palatal expansion, with an expansion part that has at least two expansion elements spaced apart from each other that are adjustable along a longitudinal axis and with two anchoring parts that are each fastened to a respective expansion element, wherein each anchoring part that is divided into two subsections by the longitudinal axis has at least one palate rest and at least one tooth support in each of the two subsections, wherein each palate rest has a support surface for contacting the palate and at least one through hole provided in the region of the support surface to accommodate a fastening element for anchoring to a palatine bone of the palate, wherein each tooth support has a first contact surface for an in particular palatal side surface of a tooth and a second contact surface, which overhangs the first contact surface and forms an in particular occlusal tooth rest for this tooth, in order to thus position the support surfaces against the palate.

DESCRIPTION OF THE PRIOR ART

A wide variety of distractors for palatal expansion are known from the prior art. In all of these distractors, an anchor in a patient's oral cavity is provided and an expansion part of the distractor exerts an expansion force on the anchor in order to thus widen the palate.

For example, US 2016/0270884 A1 discloses a distractor that is anchored to the teeth. This has the disadvantage, however, that the expansion force is limited due to the hold of the teeth in the jaw, which limits its application to patients who are still growing and whose palatal suture has not yet completely ossified.

More powerful expansion forces on the palate—for example in adults—can be achieved with distractors that are anchored to the palate by means of bone screws, as is known from US 2009/01369620 A1. To achieve this, the distractor rests with a support surface against the palate, which support surface is fastened to the palate by means of bone screws. These tensile forces, however, are disadvantageously subject to strict limits in order on the one hand to provide a sufficient fixing of the distractor to the palatine bone and on the other, to not overstress the palatal mucosa since this can lead to significant inflammation reactions throughout the oral cavity. These distractors also require an exact axial positioning relative to the palatal suture in order to thus be able to exert a uniform expansion force over the length of the palatal suture.

To facilitate such an axial positioning of distractors, DE 102016 121296 B3, for example, has disclosed a distractor with a combination of tooth anchoring and palate anchoring. Similarly operating distractors are referred to as MARPE (miniscrew aided rapid palatal expansion) or MSE (maxillary skeletal expander), etc.

Another distractor of this design type is known as the "Power Expander" created by Mr. Juan Carlos Perez Varela, which has been used as the basis for the preamble to claim 1. This distractor, which is anchored to the palate by means of four bone screws, has two tooth supports on each of the two anchoring parts, which, in addition to a palatal contact surface, also constitute an occlusal tooth rest. To achieve this, the occlusal tooth rest overhangs the palatal contact surface. This tooth support of the "Power Expander" distractor—as is known to the same degree from the other distractors—facilitates the positioning in the oral cavity or more precisely, against the palate. But even with this "Power Expander" solution, there is the risk of overstressing the palate or more precisely the palatal mucosa at the support surface, which leads to inflammation reactions in the region of the support surface and can adversely affect the healing process to a significant degree.

SUMMARY OF THE INVENTION

The object of the invention, therefore, on the basis of the prior art explained at the beginning, is to develop a distractor for palatal expansion such that despite comparatively powerful expansion forces on a palatal suture, it can be used safely and with a reduced risk of inflammation reactions.

If the anchoring parts each have at least two tooth supports, and each subsection has at least one of the tooth supports and at least one of the palate rests to which this tooth support is connected, then the support surfaces can be fixed in their position against the palate in a particularly advantageous way. Specifically by contrast with other palate-anchored distractors, the two tooth supports insure that even in response to the tensile forces of one or more bone screws, a support surface cannot move farther in the direction of the palate or more precisely, press against the palatal mucosa in an undesirable way. It is thus possible to eliminate fastening-induced compressive strains on and crushing of the palatal mucosa and the associated inflammation reactions in the region of the support surfaces. The distractor according to the invention can therefore enable the desired healing process in a reproducible way.

This position-fixing also facilitates the anchoring of the distractor since as the bone screws are tightened, the through hole of the palate rest acts as a stop and thus always insures a correct fastening to the palate. The distractor according to the invention is therefore not only able to insure the desired healing process, but can also be anchored in a comparatively user-friendly way. This also increases the treatment safety—primarily when comparatively powerful expansion forces are required, for example in order to widen the palate of an in particular adult human patient.

It should be noted in general that the tooth supports can be part of a rail piece or can also be embodied individually. In general, it is also conceivable, for example, for an in particular direct connection to be embodied by means of an arm or connector piece or a plurality of arms or connector pieces. As an in particular direct connection, it is also conceivable for a plate to be provided, for example in that this plate connects the two tooth supports to the palate rest. It should also be noted that the expressions "in particular," "particularly," and "more particularly" should be understood to mean "for example."

The position-fixing of the support surface can be insured, even with comparatively powerful tightening forces of the bone screws, if palate rests and tooth supports of the respective anchoring part are rigidly connected to each other—for example in such a way that no deformation occurs while the distractor is being anchored to the palate.

Preferably, in each anchoring part, the palate rests and tooth supports are rigidly connected to each other in a direct way. This direct connection can be embodied, for example, in the form of one or more arms. It is also conceivable for a plate to be provided as a direct connection.

Preferably, the connection between the palate rest and tooth support of the respective anchoring part is embodied as extending in such a way that it does not contact the palate in order to prevent undesirable stresses on the palatal mucosa, which can further improve the use safety of the distractor. In addition, this can be helpful for achieving an improved wearing comfort of the distractor.

Preferably, the anchoring part has a first and second arm, which each connect a tooth support to a palate rest. The distractor can therefore be easily grasped and/or positioned, which therefore further simplifies the use of the distractor.

If the palate rest is embodied as an eyelet, then this can additionally simplify the use of the distractor and simplify the design of the distractor.

If the anchoring part has a first and second arm, which each connect a tooth support to a palate rest, then this mechanical coupling can further improve the position-fixing of the palate rest against the palate, particularly if the tooth support and palate rest are connected directly. This also offers the possibility of fastening the palate rest to the tooth support at any inclination in order to thus be able to follow different palate contours. Among other things, this can contribute to an improved anchoring to the palatine bone.

The latter is particularly the case if the palate rest adjoins the first or second arm directly. In addition, this can lead to a particularly rigid mechanical connection between the tooth support and palate rest, which can improve the durability of the position-fixing.

The use of the distractor can be further facilitated if the tooth support has a third arm that connects the palate rests directly and that is firmly connected to the respective expansion element. In addition, this permits simplification of the design of the distractor. In addition, the adaptability of the palate rest to a wide variety of inclinations can be increased in order to thus be able to follow different palate contours.

Alternatively to a plurality of arms, the connection can also have a connector piece. To accomplish this, in each anchoring part, the tooth supports are connected to the palate rests by means of a shared connector piece. Consequently, these two subsections of the respective anchoring part also share this connector piece. Among other things, this makes it possible to reduce the material expense of the anchoring part.

If the connector piece is divided into two legs, which are each connected to a palate rest, then the design of the anchoring part can be further simplified. This also makes it possible to achieve a slender anchoring part for a minimized palate coverage, which can, for example, improve the wearing comfort.

If the legs extend in a V shape in relation to each other, then this can benefit the slender design of the anchoring part even more.

This is even more the case if the respective expansion element adjoins the connector piece, which splits into the two legs in this region.

Preferably, each of the anchoring parts has two palate rests and/or two, three, or four tooth supports in order to thus be able to position and also anchor the distractor in an unstressed way.

The design can be further simplified if the first tooth support has a molar band, which constitutes the first contact surface.

The use of the distractor can be further improved if the second tooth support has a half-lingual band that constitutes the first contact surface.

If the anchoring parts are embodied of one piece, more particularly embodied of one piece by means of an additive production method, then by means of a comparatively high geometrical accuracy, this insures an exact positioning and fixing of the distractor against the palate.

The mechanical resilience of the distractor can be further improved if the anchoring part consists of a cobalt-chromium-tungsten alloy, more particularly Co63.9Cr24.7W5.5Mo5.0Si.

The fixing of the support surfaces in their position against the palate can be improved if tooth supports of the two anchoring parts situated the farthest toward the outside relative to the longitudinal axis define a support plane between themselves, within which the palate rests are positioned. For example, this can durably prevent a tilting while the distractor is being fixed in position with palatal screws. The risk of an overstressing of the palate or more precisely of the palatal mucosa at the support surface therefore cannot occur and adversely affect the healing process.

In order to fix the position of the support surfaces against the palate, it can be sufficient if the first tooth support of each anchoring part is embodied so that it can be provided at a molar and/or the second tooth support of each anchoring part is embodied so that it can be provided at a premolar.

In order to fix the position of the support surfaces against the palate, it can be sufficient if the first tooth support of each anchoring part is embodied so that it can be provided at a first tooth, which is a molar, and/or the second tooth support of each anchoring part is embodied so that it can be provided at a second tooth, which is a premolar.

Preferably, the support surfaces of the palate rests are each embodied so that they follow the contour of the palate, more particularly of the palatal mucosa, which can further improve the desired course of treatment.

Preferably, the tooth supports are each embodied so that they follow the contour of the relevant tooth, which can further improve the wearing comfort of the distractor.

Another object of the invention is to create a method with which the distractor according to the invention can be produced in a geometrically accurate way.

If a digital image is taken of at least one section of a patient's jaw, the support surfaces and tooth supports are adapted to the digital image and, with the aid of an additive production method, the anchoring parts are produced with the adapted support surfaces and tooth supports, then this permits a particularly high degree of fit accuracy of the distractor in relation to the respective jaw and palate of the respective patient. In particular, this can insure the desired course of treatment.

BRIEF DESCRIPTION OF THE DRAWINGS

The subject of the invention is shown in greater detail by way of example in the drawings based on a plurality of embodiment variants. In the drawings.

WAYS TO IMPLEMENT THE INVENTION

Figure 1:
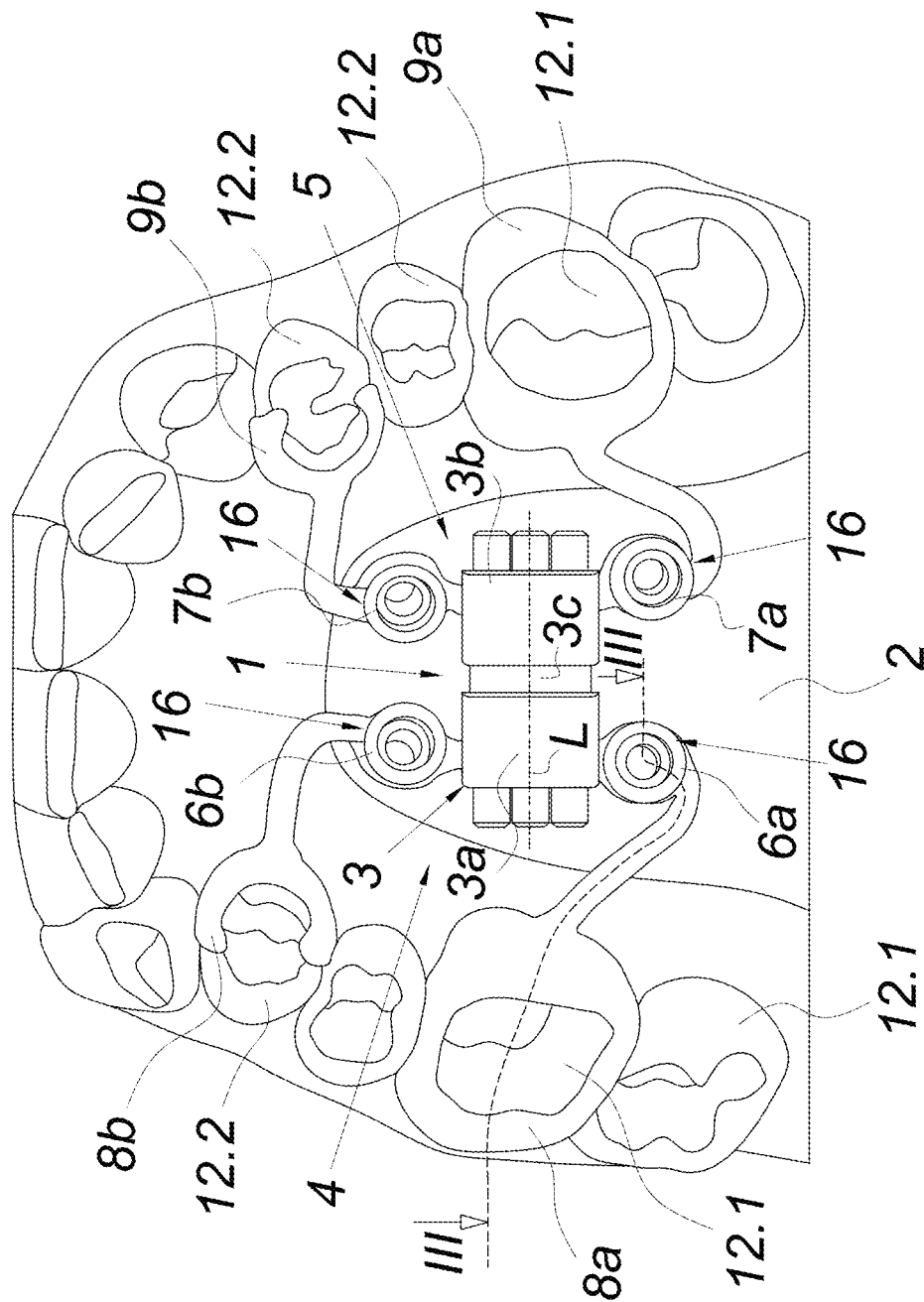
FIG. 1 shows a top view of a first distractor positioned against a palate according to a first embodiment variant.

FIG. 1 shows the distractor 1 according to the invention in a first embodiment variant without fastening elements, which is positioned against a simulation of a palate 2 and dental arch.

The distractor 1 has an expansion part 3 with two expansion elements 3*a*, 3*b* that can be adjusted in their distance from each other. This adjustment along a longitudinal axis L of the expansion part 3 is performed by means of a spindle drive 3*c*, which engages the two expansion elements 3*a*, 3*b*.

The distractor 1 also has two anchoring parts 4, 5 with a plurality of palate rests 6*a*, 6*b*, 7*a*, 7*b* and a plurality of tooth supports 8*a*, 8*b* and 9*a*, 9*b*, respectively. The anchoring parts 4, 5 are each firmly connected or fastened to an expansion element 3*a*, 3*b* of the distractor 1.

The plurality of palate rests 6*a*, 6*b*, 7*a*, 7*b*, four in the exemplary embodiment, are used for anchoring the distractor 1 to the palate 2. In each anchoring part 4 and 5, respectively, two palate rests 6*a*, 6*b* and 7*a*, 7*b*, respectively, are provided, namely a respective palate rest 6*a*, 6*b*, 7*a*, and 7*b* in each subsection 4*a*, 4*b* and 5*a*, 5*b*, respectively, of the respective anchoring part 4 and 5, respectively, wherein the two subsections 4*a*, 4*b* and 5*a*, 5*b*, respectively, are produced by means of a division of the respective anchoring part 4 and 5, respectively, at the longitudinal axis L of the expansion part 3, which is shown in greater detail in FIG. 2.

Figure 2:
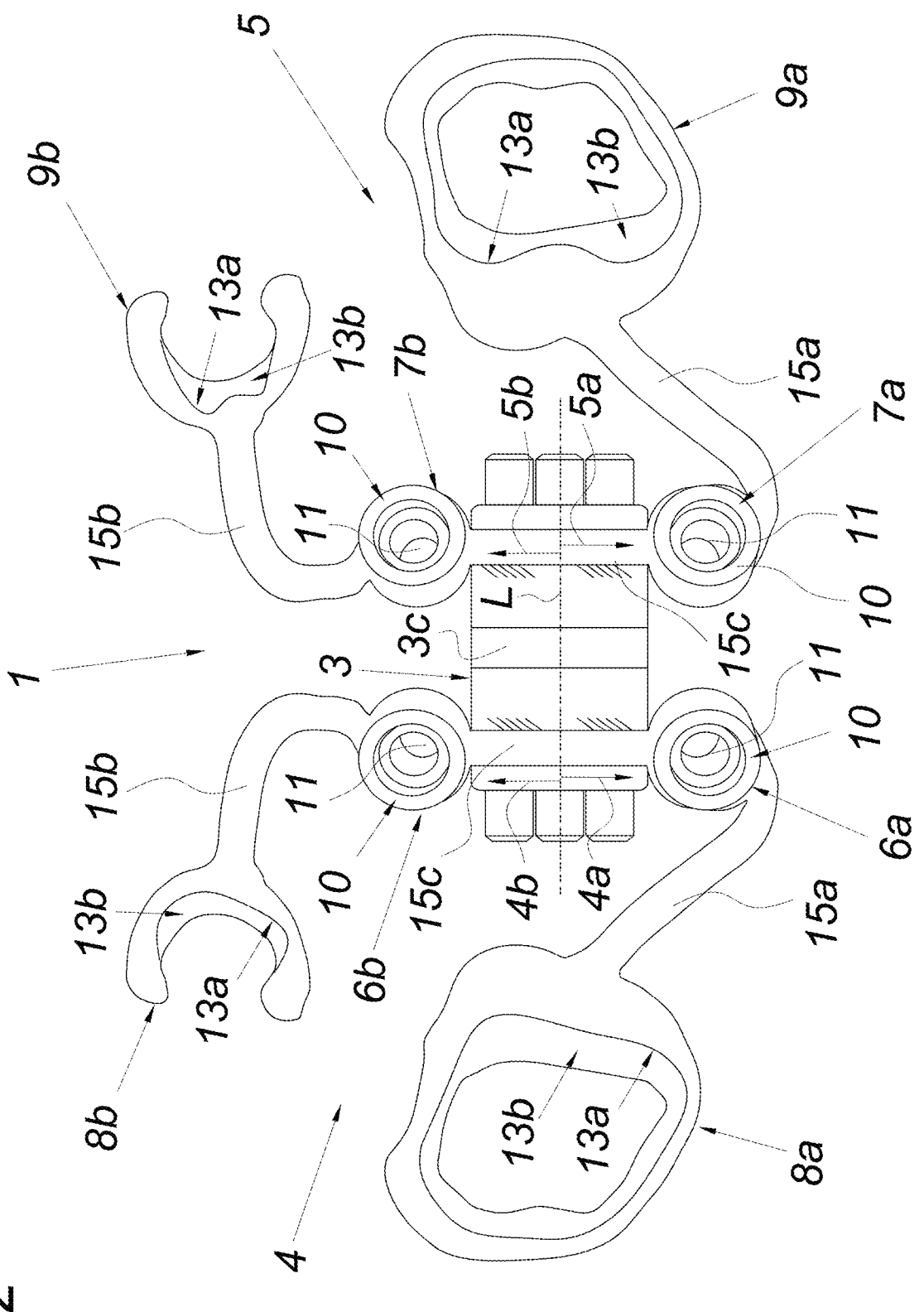
FIG. 2 shows a bottom view of the distractor shown in FIG. 1.

In addition, the palate rests 6*a*, 6*b*, 7*a*, 7*b* each have a support surface 10 by means of which the distractor 1 rests against the palate 2 or more precisely, against the palatal mucosa. These ring-shaped support surfaces 10 are shown in FIG. 2. In addition, in the region of the support surfaces 10 of the palate rests 6*a*, 6*b*, 7*a*, 7*b*, a respective through hole 11 is provided, through which—as shown for example in FIG. 3—four bone screws 100 used as fastening elements anchor the distractor 1 to the palate 2.

So that this anchoring takes place in a precisely positioned way relative to the palate 2, the distractor 1 has a plurality of tooth supports 8*a*, 8*b* and 9*a*, 9*b*, respectively.

Figure 3:
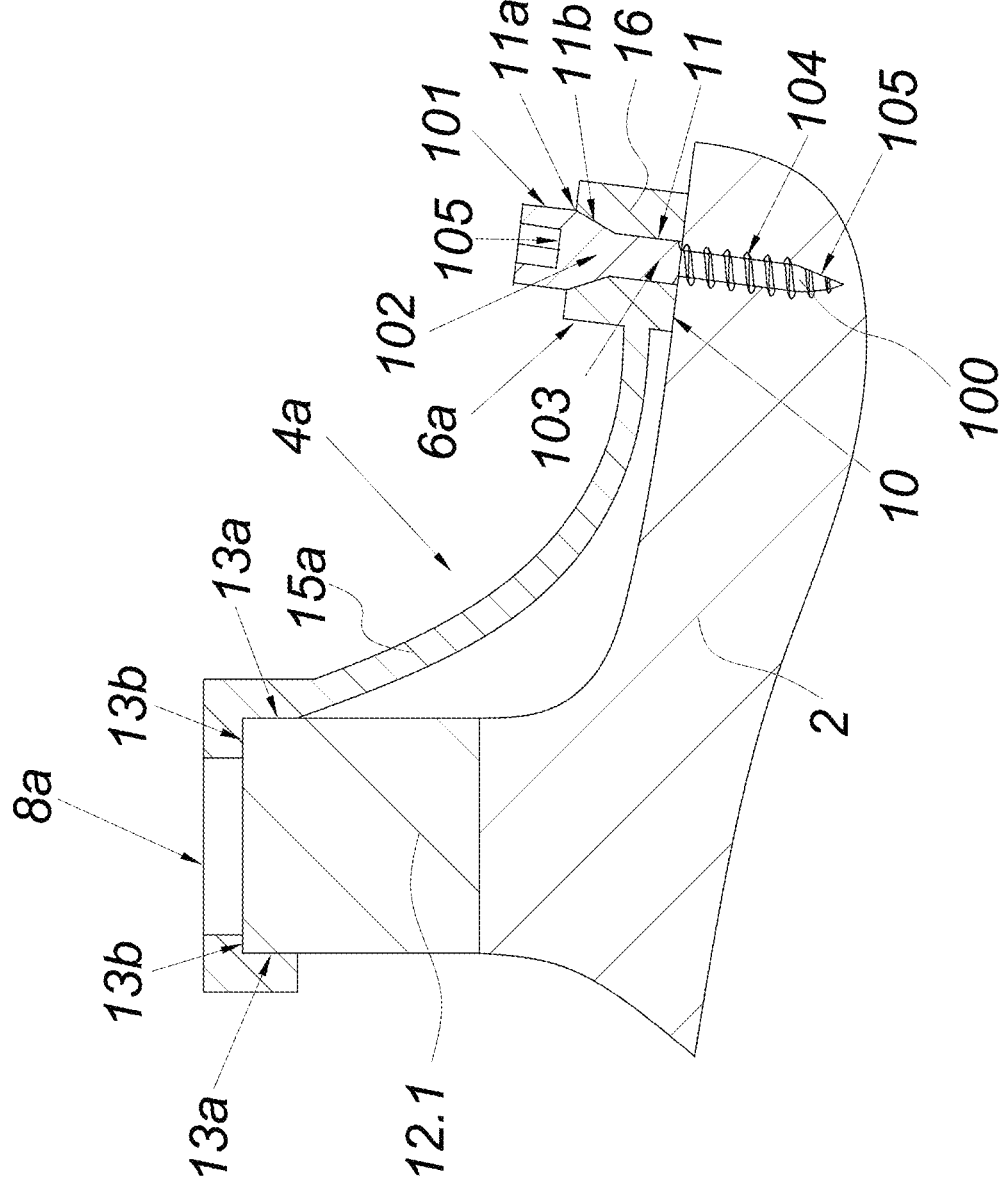
FIG. 3 shows a side view cut away along the axis III-Ill of the distractor in FIG. 1.

Of these, each tooth support 8*a*, 8*b*, 9*a*, 9*b* has a first contact surface 13*a* for a palatal side surface of a first tooth 12.1, which is a molar, and a second contact surface 13*b*, which overhangs the first contact surface 13*a* and forms an occlusal tooth rest for this tooth 12.1—in particular, see FIG. 3 in this regard. By means of these tooth supports 8*a*, 8*b*, 9*a*, 9*b*, the support surface 10 can now be positioned against the palate 2—and thus the distractor 1 can be aligned relative to the palate 2.

According to the invention, this contact of the support surfaces 10 against the palate 2 is also fixed in position by virtue of the fact that the anchoring parts 4, 5 each have at least two tooth supports 8*a*, 8*b*, 9*a*, 9*b*, each for a respective tooth 12.1, 12.2, and in each subsection 4*a*, 4*b* and 5*a*, 5*b*, respectively, at least one tooth support 8*a*, 8*b*, 9*a*, 9*b* is connected to a respective palate rest 6*a*, 6*b*, 7*a*, 7*b*—in particular, see FIGS. 1, 2 and 4, 5, respectively, in this regard.

Both subsections 4*a*, 4*b* and 5*a*, 5*b*, respectively, of the respective anchoring part 4 and 5, respectively, therefore each have a tooth support 8*a*, 8*b*, 9*a*, 9*b* and a palate rest 6*a*, 6*b*, 7*a*, 7*b* and are thus fixed in position along with their palate rests 6*a*, 6*b* and 7*a*, 7*b*, respectively, or more precisely, the support surfaces 10 are thus fixed in their position against the palate 2.

According to FIG. 1, the tooth supports 8*a*, 8*b*, 9*a*, 9*b* on the one hand are embodied so that the first tooth supports 8*a*, 9*a* can be provided at the first tooth 12.1, which is a molar, and on the other hand, are embodied so that the second tooth supports 8*b*, 9*b* can be provided at the second tooth 12.2, which is a premolar.

A tightened fastening element therefore cannot pull the support surfaces 10 in the direction of the palate 2—thus consistently avoiding a stress on the palatal mucosa. There is thus no risk of inflammation reactions occurring in the palatal mucosa in the region of the support surfaces 10, which can adversely affect the healing process to a significant degree.

This is particularly the case because the support surfaces 6*a*, 6*b*, 7*a*, 7*b* of the palate rests are each embodied so that they follow the respective contour of the palatal mucosa of the palate 2, specifically in the places where they respectively rest against the palate 2. The wearing comfort of the distractor 2 is particularly high because the tooth supports 8*a*, 8*b*, 9*a*, 9*b* are each embodied so that they follow the contour of the relevant tooth 12.1, 12.2.

This design embodiment according to the invention also offers the possibility of positioning the through holes 11 of the palate rests 6*a*, 6*b*, 7*a*, and 7*b* relative to one another in a particular way. For example, these through holes 11 can be provided within a molar box (or more precisely, in the section of the palate between the opposing molar teeth) and can each be positioned the same distance from the midpalatal suture of the upper jaw on the distractor 1. This insures a reliable treatment success.

As is clear from FIG. 1, the palate rest 6*a*, 6*b*, 7*a*, 7*b* and tooth support 8*a*, 8*b* and 9*a*, 9*b*, respectively, are rigidly connected to each other directly by means of a first arm 15*a* and second arm 15*b*, respectively. As a result, the palate rests 6*a*, 6*b*, 7*a*, 7*b* can also be provided with different inclination angles relative to the palate 2 and are thus particularly adaptable to the curvature of the palate 2. In particular, they can also be adjusted in their inclination so that the fastening elements overlap more with the palatine bone and thus improve the fixing of the distractor 1 in position.

In a simply designed embodiment, the palate rests 6*a*, 6*b*, 7*a*, 7*b* in the form of an eyelet 16 adjoin the arm 15*a*, 15*b* directly. The palate rests 6*a*, 6*b*, 7*a*, 7*b* of the anchoring part 4 and 5, respectively, are each adjoined by a third arm 15*c*—as shown in FIG. 2.

This third arm 15*c* is firmly connected to the respective expansion element 3*a*, 3*b*—specifically integrally joined by means of welded connections that are schematically depicted in FIG. 2. As a result, the anchoring parts 4 and 5, respectively, can be embodied of one piece independently of the expansion part 3, for example by means of an additive production method. An exact adaptation of the anchoring parts 4 and 5, respectively, to the palate 2 is therefore possible. Preferably, at least the support surfaces 10 or the anchoring parts 4 and 5, respectively, are electropolished. Preferably, the anchoring parts 4, 5 are made of a cobalt-chromium-tungsten alloy—preferably of Co63.9Cr24.7W5.5Mo5.0Si.

FIG. 2 also shows that the first tooth support 8*a*, 9*a* of an anchoring part 4 and 5, respectively, has a molar band, which constitutes the first contact surface 13*a*. The molar band is adjoined by the occlusal tooth rest. The second tooth support 8*b* and 9*b*, respectively, of an anchoring part 4 and 5, respectively, has a half-lingual band that constitutes the first contact surface 13*a*. The half-lingual band is adjoined by the occlusal tooth rest 13*b*.

The four bone screws 100 provide for a user-friendly anchoring of the distractor 1. Each bone screw 100 engages the through hole 11 of the respective tooth support 8*a*, 8*b*, 9*a*, 9*b*, wherein the through hole 11 has an end section 11*b* tapering conically from the hole edge 11*a*, as shown for example for the tooth support 8*a* in FIG. 3.

This end section 11*b* serves as a stop for the bone screw 100, namely as a stop for a truncated cone-shaped head section 102 on the screw head 101 of the bone screw 100. An overtightening of the bone screw 100 therefore cannot take place. Preferably, the tooth supports 8a, 8b, 9a, 9b are glued to the respective tooth and then the distractor 1 is anchored to the palate 2 with the bone screws 100.

The bone screw 100 also has an external thread 104 on the shaft 103 and a flattened region at the shaft end. The bone screw 100 also has an internal cone 105 in the head, via which the bone screw 100 can be actuated in a user-friendly way.

Figure 4:
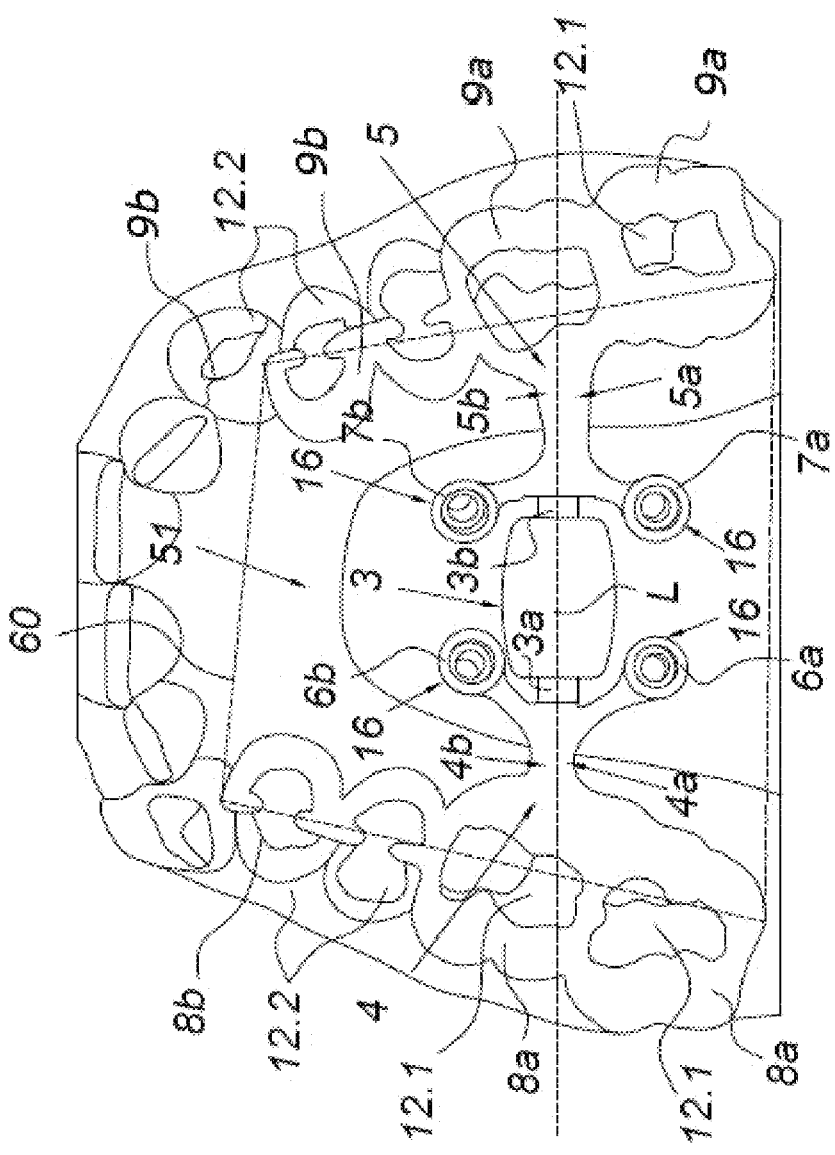
FIG. 4 shows a top view of a second distractor, positioned against a palate according to a second embodiment variant.
Figure 5:
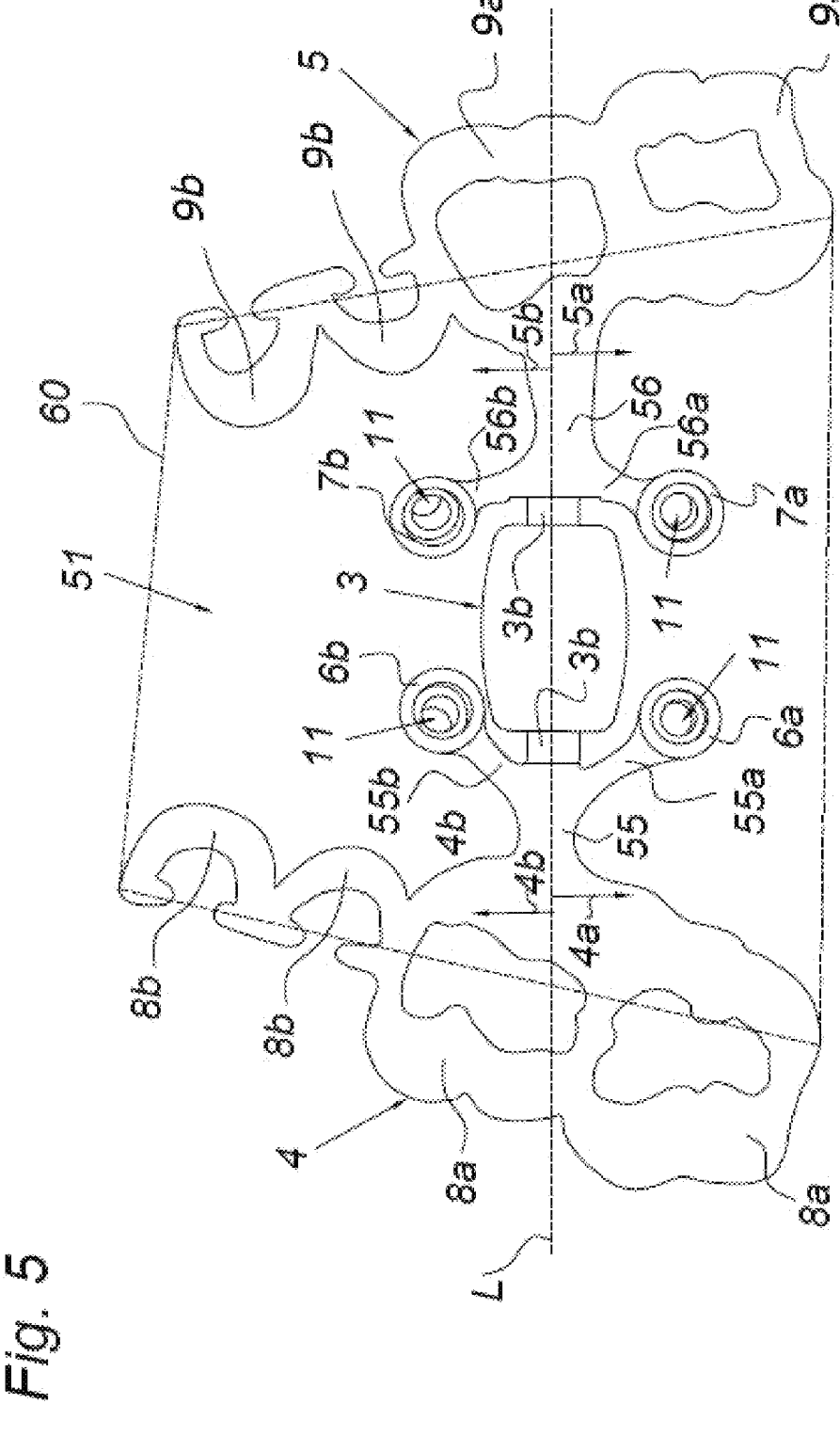
FIG. 5 shows an enlarged top view of the distractor according to FIG. 4.

FIG. 4 and FIG. 5 show top views of another distractor 51 according to the invention in a second embodiment variant without fastening elements.

By contrast with the distractor 1 In FIGS. 1 and 2, the anchoring parts of the distractor 51 have differently designed anchoring parts 4, 5. As a result, they have a differently embodied connection between the respective tooth supports 8a, 8b and 9a, 9b, respectively, and the palate rests 6a, 6b and 7a, 7b, respectively.

In this case, each anchoring part 4, 5 is provided with a shared connector piece 55 and 56, respectively, which leads from the tooth supports 8a, 8b and 9a, 9b, respectively, adjoins the respective expansion element 3a, 3b, and splits there into two legs 55a, 55b and 56a, 56b, respectively, which each adjoin a palate rest 6a, 6b and 7a, 7b, respectively, as can be seen particularly in FIG. 5.

These connections between the respective tooth supports 8a, 8b and 9a, 9b, respectively, and the palate rests 6a, 6b and 7a, 7b, respectively, are embodied as Y-shaped, which produces particularly compact anchoring parts 4, 5. Among other things, this increases the wearing comfort of the distractor 51.

In addition, the distractor 51 has four tooth supports 8a, 8b and 9a, 9b, respectively, per anchoring part 4, 5, which results in a particularly broad support plane 60. This support plane 60 is defined between the tooth supports 8a, 8b, 9a, 9b of the two anchoring parts 4, 5 that are situated the farthest toward the outside relative to the longitudinal axis L. The palate rests 6a, 6b, 7a, 7b are situated within the support plane 60, which results in a highly stable position-fixing of the distractor or more precisely, of the palate rests 6a, 6b, 7a, 7b, relative to the palate.

But in this distractor 51, the anchoring parts 4, 5 also each have at least two, namely four, tooth supports 8a, 8b, 9a, 9b. In a way that is comparable to the distractor 1, each subsection 4a, 4b and 5a, 5b, respectively, of the anchoring parts 4, 5 in this case also has at least one of the tooth supports 8a, 8b and 9a, 9b, respectively, and at least one of the palate rests 6a, 6b and 7a, 7b, respectively. In this case, the first subsection 4a, 5a has one first tooth support 8a at a first tooth 12.1 and the second subsection 4b, 5b has two second tooth supports 8b, each at a second tooth 12.2. A first tooth support 8a at a tooth 12.1 is a feature that is common to both of these subsections 4a, 5b.

In addition, three tooth supports 8a, 8b and 9a, 9b, respectively, per anchoring part 4, 5 can be provided, which is not shown in detail.

For the production of a distractor 1, 51, a digital image is advantageously taken of a patient's jaw. The support surfaces 10 and tooth supports 8a, 8b, 9a, 9b are adapted to the digital image of the jaw, by means of which the distractor 1, 51 can insure a high degree of fit accuracy. Preferably, with the aid of an additive production method, the anchoring parts 4, 5 are produced with the adapted support surfaces 10 and tooth supports 8a, 8b, 9a, 9b, which simplifies the production process and accelerates the production of the distractor 1, 51 while nevertheless achieving a high degree of individuality based on different jaw shapes.

8

The invention claimed is:

1. A distractor for palatal expansion, comprising:
an expansion part that has at least two expansion elements spaced apart from each other that are adjustable along a longitudinal axis and
two anchoring parts that are each fastened to a respective expansion element, wherein each anchoring part of the two anchoring parts that is divided into two subsections by the longitudinal axis has at least one palate rest and at least one tooth support in each of the two subsections,
wherein each palate rest of the at least one palate rest has a support surface for contacting a palate and at least one through hole provided in a region of the support surface to accommodate a fastening element for anchoring to a palatine bone of the palate,
wherein each tooth support of the at least one tooth support has a first contact surface for contacting at least a portion of a palatal side surface of a tooth and a second contact surface for contacting at least a portion of an occlusal surface of the tooth, wherein the second contact surface overhangs the first contact surface and forms an occlusal tooth rest, in order to thus position the support surfaces against the palate,
wherein each of the two anchoring parts has at least two tooth supports and wherein each subsection has at least one of the tooth supports and at least one of the palate rests to which this tooth support is connected in order to thus fix the support surfaces in their position against the palate, and
wherein in each anchoring part, each of the at least one tooth support is connected to the palate rests by a shared connector piece, and the connector piece splits into two legs, which each adjoin a palate rest of the at least one palate rest.

2. The distractor according to claim 1, wherein the palate rests and the tooth supports of the respective anchoring part are directly connected to each other in a rigid way.

3. The distractor according to claim 1, wherein a connection between the palate rests and each of the at least one tooth support of the respective anchoring part extends in such a way that the connection does not contact the palate.

4. The distractor according to claim 1, wherein the at least one palate rest is an eyelet.

5. The distractor according to claim 1 wherein the two legs extend in a V shape in relation to each other and/or the respective expansion element adjoins the connector piece, which splits into the two legs in this region.

6. The distractor according to claim 1, wherein each of the anchoring parts has two palate rests and/or two, three, or four tooth supports.

7. The distractor according to claim 1, wherein a first tooth support has a molar band, which constitutes the first contact surface.

8. The distractor according to claim 7, wherein a second tooth support has a half-palatal band that constitutes the first contact surface.

9. The distractor according to claim 1, wherein each of the two anchoring parts is embodied of one piece by means of an additive production method.

10. The distractor according to claim 1, wherein the through hole has an end section tapering conically from a hole edge.

11. The distractor according to claim 1, wherein each of the two anchoring parts consists of a cobalt-chromium-tungsten alloy.

12. The distractor according to claim 1, wherein each of the at least one tooth support of the two anchoring parts situated farthest toward an outside relative to the longitudinal axis defines a support plane between themselves, within which the palate rests are positioned.

13. The distractor according to claim 1, wherein a first tooth support of each anchoring part is embodied so that it can be provided at a first tooth, which is a molar, and/or a second tooth support of each anchoring part is embodied so that it can be provided at a second tooth, which is a premolar.

14. The distractor according to claim 1, wherein the support surfaces of the palate rests follow a contour of the palate and/or the tooth supports follow a contour of the relevant tooth.

15. A bone screw for the distractor according to claim 1, wherein at a screw head, the bone screw has a truncated cone-shaped head section, which extends from a shaft of the bone screw.

16. A method for producing the distractor according to claim 1, comprising taking a digital image of at least one section of a patient's jaw, and adapting the support surfaces and tooth supports to the digital image and, using an additive production method to produce the two anchoring parts with the adapted support surfaces and tooth supports.

\* \* \* \* \*